United States Patent [19]

Schenk

[11] Patent Number: Plant 6,448

[45] Date of Patent: Dec. 6, 1988

[54] LILIUM 'PARISIENNE'

[75] Inventor: Peter Schenk, Wieringerwerf, Netherlands

[73] Assignee: Bischoff Tulleken Leliecultuur B.V., Wieringerwerf, Netherlands

[21] Appl. No.: 10,008

[22] Filed: Feb. 2, 1987

[51] Int. Cl.[4] ..... A01H 5/00

[52] U.S. Cl. ..... Plt./68

[58] Field of Search ..... Plt./68

*Primary Examiner*—James R. Feyrer

*Attorney, Agent, or Firm*—Eugene D. Farley

[57] ABSTRACT

A new variety of Asiatic hybrid lily plant, particularly distinguished by its large flowers, unusual color and long persistence, both on the plant and as cut flowers.

It is characterized by its regular and attractive inflorescence, the greenish/pink color of its buds, the large flowers, the special way of its tepal spotting and the brilliant salmon pink color of its flowers with an apricot yellow throat.

1 Drawing Sheet

BACKGROUND AND GENERAL STATEMENT OF THE INVENTION

My new variety of lily plant is classified botanically as a Lilium Hybrid, commercially as an upright Asiatic hybrid Division 1 A in the Horticultural Classification of the Genus Lilium adopted by The Royal Horticultural Society of London.

My new variety of lily plant originated as a seedling selected from a group of seedlings of test crosses at Bischoff Tulleken Leliecultuur B.V., Wieringerwerf, Holland.

The breeding program was initiated in 1977 and the lily plant first flowered in 1980.

The cross was made during a breeding program having as its objective the production of pink unspotted or lightly spotted, upright flower cultivars which would perform adequately when forced into flower under glass throughout the year, in addition to meeting the requirements of vigor, disease resistance and rapid natural propagation in field growth.

Cultivars were sought which would be disease resistant, virus tolerant and not overly susceptible to leaf scorch or bud abortion when forced under glass. The cross was made between the seed parent 'Sundrop' and the pollen plant was 'Scout'. Neither parent is patented.

My new plant is characterized by rapid and natural propagation under field conditions and by vigorous and healthy growth when forced under glass without leaf scorch and abortion.

My new variety of lily plant has been asexually reproduced by me at Bischoff Tulleken Leliecultuur B.V., Wieringerwerf, Holland.

Successive generations produced by bulbscale propagation and natural propagation from bulblets have demonstrated that the novel and distinctive characteristics of my new variety are fixed and hold true under propagation from generation to generation.

THE DRAWING

My new variety of lily plant is illustrated in the accompanying photographic drawing which shows the plant, its foliage and its buds in their various stages of development and the open bloom in full color.

DESCRIPTION OF THE NEW VARIETY

The following is a detailed description of my new variety of the Asiatic hybrid lily with nomenclature according to the International Lily Register and with color designations according to The Royal Horticultural Society Color Chart (R.H.S.C.C.)

The Plant

Form: *Bulbous monocotyledon.*

Height: Bulbs 12–16 cm in circumference produce stems: 70–90 cm (28–36") tall when forced flower under glass; Field grown bulbs produce stems: 60–80 cm (24–32") tall in their second season after scaling.

Growth: Very vigorous and strong.

Foliage: Abundant with about 80–100 leaves per stem.

Size of leaves: 8–12 cm (3.2–4.8") long, 1.0–1.5 cm (0.4–0.6") wide.

Shape of leaves: Lanceolate.

Texture of leaves: Leaves entire (not serrated) smooth and glossy on upper sides and lower sides.

Color of leaves: Upperside: medium green. Underside: medium to dark green.

Ribs and veins of leaves: Typical monocotyledonous venation; light green parallel veins.

Stem: Green.

Inflorescence

Well spaced pyramidal raceme with ascending pedicels and no secondary buds. Bulbs which are 12–15 cm (4.8–6") in circumference produce 5–7 buds.

cir

Peduncle and pedicel: Smooth and glossy. Buds are big and smooth.

Color of inflorescence: light green with soft green/-pinkish overlay.

The Buds

Size: 7–9 cm (3–3¼') long, 2–5 cm (0.8–2") wide.

Form: Lanceolate with obtuse tip; typical of Asiatic hybrid lilies.

Open slowly: Open in about one hour in response to (morning) light. Flowers further up the stem open on subsequent days over an interval of 1–2 weeks.

Color of mature buds: Brilliant green/pinkish. The color turns more pink when the bud matures.

The Flower

Blooming characteristics: Flowers in mid-season, late June and early July in The Netherlands, once, and profusely.

Flower size: Flower diameter is 12–15 cm (4.8–6″). Inner tepals are 3.0–3.5 cm (1.2–1.4″) wide. Outer tepals are 2.0–2.5 cm (0.8–1″) wide.

Shape when flower first opens: Shallow bowl-shape with lightly recurved tepal tips. Tepals recurve more as flower ages.

Tepal arrangement: Typical of the genus Lilium, with 6 entire imbricated tepals.

Color, outer tepals: When fully opened the color is carmine pink R.H.S. C.C. 50B. Throat is apricot yellow R.H.S. C.C. 24D with light orange areas R.H.S. C.C. 24A.

Color, base of tepals: The base of the tepals is soft reddish R.H.S. 33D.

Color, inside tepals: Color is carmine pink R.H.S. C.C. 50B. Throat is apricot yellow R.H.S. C.C. 24D. with light orange spots R.H.S. 24A.

Color, reverse of tepal: The color of the reverse is R.H.S. C.C. 38A with a light green midrib.

Spotting pattern: A few tiny spots dark brown spread over the middle part of the flower.

Tepal duration: Tepals remain on individual flower for 5–7 days. Stem has flowers with tepals adhering for about 3 weeks. Tepals fall as flower ages.

Flower texture: Good texture. Not affected by high temperatures or wet conditions.

The Flower

Pedicel: Pedicel is sturdy and upright, ascending at 60° angle.

*Length.*—5–12 cm (2–5″).

*Color.*—Green.

Fragrance: None.

Last quality: Flowers remain on plants for about 2–3 weeks. Flowers remain on cut flower stem for about 2 weeks with adequate light.

The Reproduction Organs

Stamens and anthers: Typical of genus Lilium. Six versatile anthers hang (singly) from 6 narrow filaments.

Filaments: 5–6 cm (2″) long and light pink.

Pollen: Reddish brown.

Pistil: 1, typical of genus Lilium. Style is 5–6 cm (2″) long.

Stigma: Small, light reddish gray.

Ovary: Typical of genus Lilium. Superior, single 6 chambered ovary.

The Fruit

Fertile, capsule is oblong with 6 chambers.

Color at maturity is medium green to dark green, sometimes overlaid with soft purple. Fades to soft brown when fruit splits open to release seeds.

The Bulbs

Color of the bulbs: White.

Size of the bulbs: Usual commercial size is 12–20 cm (5–8″) in circumference; bulbs can be grown to a larger size if this is desired.

I claim:

1. A new and distinctive variety of Asiatic hybrid lily plant, substantially as herein shown and described, characterized by its rapid natural propagation under field conditions;
its vigorous healthy growth without leaf scorch, when forced under glass;
its regular and attractive inflorescence;
the green pinkish color of its buds;
the big size of the buds;
the large size of its flower;
the great width of its tepals,
the typical character of its tepal spotting;
the brilliant salmon pink color of its flowers with an apricot yellow throat
and the long life of its flowers.

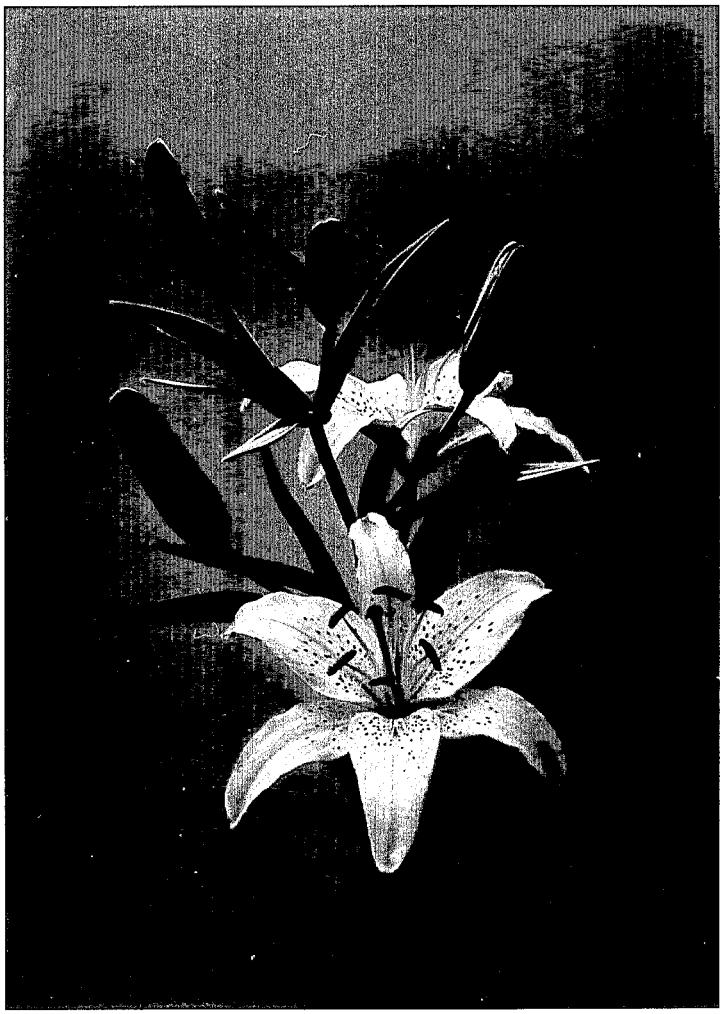

* * * * *